US00PP32530P2

(12) United States Plant Patent
Hansen

(10) Patent No.: US PP32,530 P2
(45) Date of Patent: Nov. 24, 2020

(54) ***SEDUM* PLANT NAMED 'PRIDE AND JOY'**

(50) Latin Name: ***Sedum* hybrid**
Varietal Denomination: Pride and Joy

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,785

(22) Filed: Nov. 26, 2019

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479

CPC ... A01H 5/02; A01H 5/00; A01H 5/12; A01H 6/32; A01H 6/328
See application file for complete search history.

(56) References Cited

PUBLICATIONS

Sparks Seven Plant Varieties Selected as Fan Favorites at Farwest 2019, retrieved on Jun. 15, 2020, retrieved from the Internet at https://www.greenhousegrower.com/crops/seven-varieties-selected-as-fan-favorites-at-farwest-2019/#Tinsel/147191/3,12 pp. (Year: 2019).*

* cited by examiner

*Primary Examiner* — June Hwu

(57) ABSTRACT

A new and distinct cultivar of perennial *Sedum* plant named 'Pride and Joy' is characterized by drought-tolerant, winter-hardy, dense, low, compact mounds with blue-green foliage and stems that resist opening up in the center of the plant. The flowers of a purplish-pink effect for about four weeks beginning in mid-August. The new plant is useful for landscaping as a specimen plant, en masse or in a container.

1 Drawing Sheet

Botanical designation: *Sedum* hybrid.
Cultivar denomination: 'Pride and Joy'.

STATEMENT REGARDING PRIOR DISCLOSURES UNDER 37 CFR 1.77(b)(6)

The first non-enabling disclosure of the claimed plant, in the form of a photograph and brief description was on a website operated by Walters Gardens, Inc. on Dec. 1, 2019. The claimed plant was first sold on Apr. 8, 2019 by Walters Gardens, Inc. followed by a public disclosure on May 29, 2019 in the "Walters Gardens 19-20 Catalog." Walters Gardens, Inc. obtained the new plant and all information relating thereto, from the inventor. No plants of *Sedum* 'Pride and Joy' have been sold in this country or anywhere in the world under this or any name, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of *Sedum* or Stonecrop plant, botanically known as *Sedum* and hereinafter referred to by the cultivar name 'Pride and Joy'. There are over 300 recognized species of the genus *Sedum*.

The new plant was a whole-plant mutation of *Sedum* 'Pure Joy' U.S. Plant Pat. No. 24,194 discovered by the inventor Aug. 17, 2016 display gardens of a wholesale perennial nursery in Zeeland, Mich. The new plant was initially selected in the autumn of 2016 and assigned the plant code 16-SP-SED-548 for the remainder of the trial period. 'Pride and Joy' was approved for final evaluation in the fall of 2017. Initial propagation was by basal shoot cuttings since September of 2017 at a wholesale perennial nursery in Zeeland, Mich. has shown that the unique features of this new *Sedum* plant are stable and reproduced true to type in successive generations.

SUMMARY OF THE INVENTION

Plants of *Sedum* 'Pride and Joy' have not been observed under all possible environmental conditions. The phenotype may vary somewhat with variations in environment such as temperature, available water, fertility and light intensity without, however, any variation in genotype.

The closest comparison varieties known to the inventor include: 'Pure Joy' U.S. Plant Pat. No. 24,194, 'Superstar' U.S. Plant Pat. No. 31,547, 'Bundle of Joy' U.S. Plant Pat. No. 30,808, 'Powderpuff' U.S. Plant patent application Ser. No. 16/873,097 and 'Dazzleberry' U.S. Plant Pat. No. 22,457. 'Pure Joy' has a similar habit but the flowers are a lighter pink and the leaves are not as dark and less blue-green. 'Superstar' produces seed and is not sterile, has greyed-purple foliage and the flowers are more intense purplish-pink. 'Bundle of Joy' has near white-colored flowers and identical habit to the new plant. 'Powderpuff' has a lighter brighter pink flower and is more upright in habit. 'Dazzleberry' has a smoky gray foliage overlay and the flowers are vibrant raspberry-colored. 'Mongolian Stardust' (not patented) has blue-green foliage, more open habit, and the flowers are near white.

The following traits have been repeatedly observed and are determined to be the unique characteristics of *Sedum* 'Pride and Joy'. The following characteristics in combination distinguish 'Pride and Joy' as a new and distinct Stonecrop plant unique from all other Stonecrop plants known to the inventor:

1. Short and compact plant habit;
2. Plants are drought tolerant and winter hardy to at least USDA zone 3;
3. Small leaves of blue-green;
4. Stems and foliage stay tightly compact resistant to open in center of plant;
5. Late blooming with flowers of purplish-pink;
6. Sterile flowers without seed production.

BRIEF DESCRIPTION OF THE PHOTOGRAPH

The photograph of the new plant demonstrates the unique traits and the overall appearance of *Sedum* 'Pride and Joy'. The colors are as accurate as reasonably possible with color reproductions of this type. Variations in ambient light spectrum, source and direction may cause the appearance of minor variation in color. The plants used in the photographs were three-year-old plants grown in an open, full-sun display garden at a wholesale perennial nursery in Zeeland, Mich. with supplemental water and fertilizer when needed. No plant growth regulators have been used.

DETAILED BOTANICAL DESCRIPTION

Figure 1:
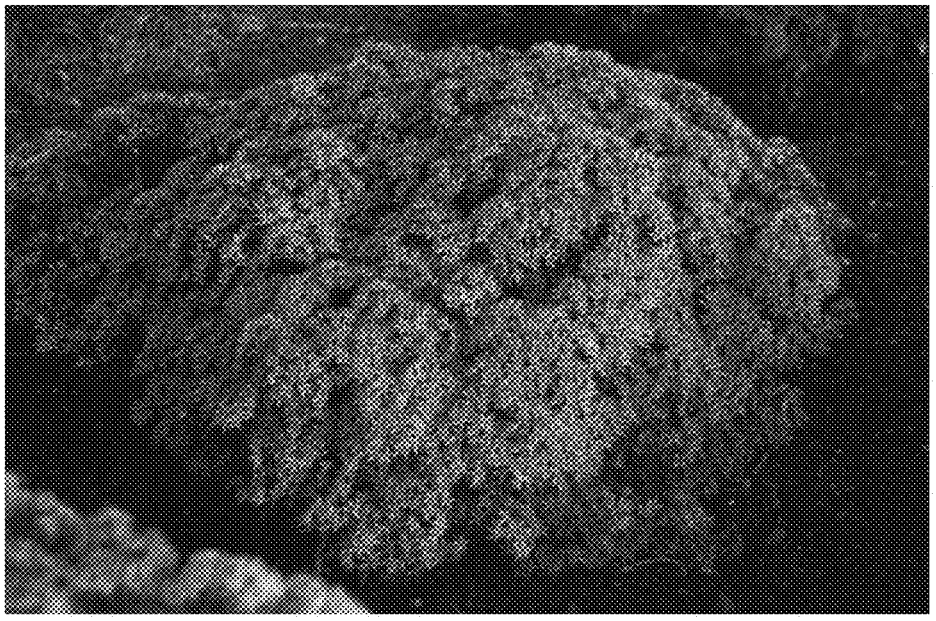
FIG. 1 shows the plant in full flower habit.
Figure 2:
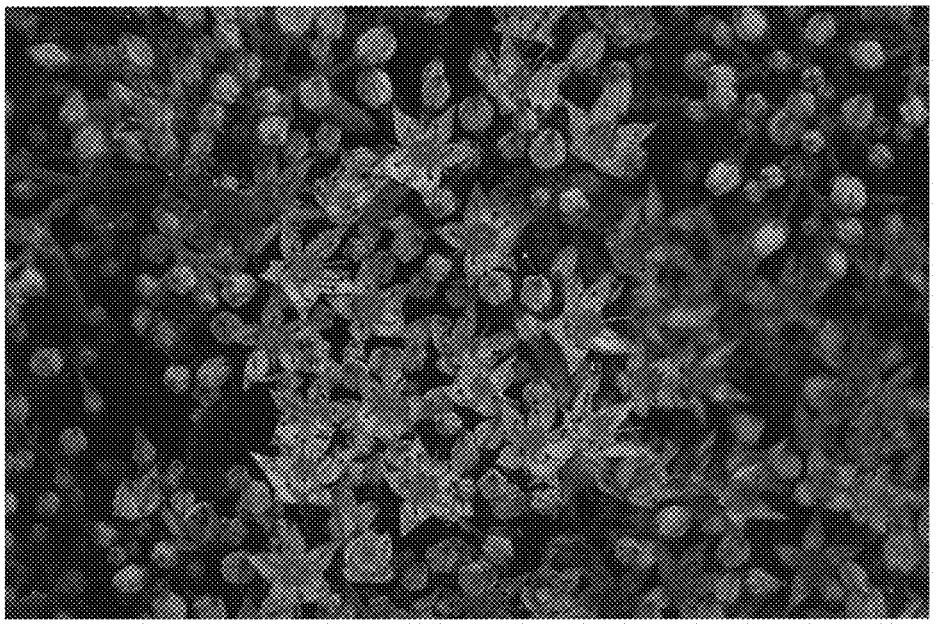
FIG. 2 shows a close-up of the plant in early flowering with foliage and buds.

The following is a detailed description of three-year-old plants of the new cultivar as grown outdoors in a full sun trial plot and also as greenhouse grown specimens at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Pride and Joy';

Parentage: A whole-plant mutation of *Sedum* 'Pure Joy';

Asexual propagation: Stem cuttings and division;

Time to initiate roots: About two weeks;

Time to finish a 3.7 liter flowering container: About three months in the summer from a rooted 2.5 cm plug;

Root description: Thick, fleshy; freely branching; creamy white to light tan in color; color nearest RHS 158D depending on soil content;

Plant habit: Winter-hardy, succulent, herbaceous perennial; low mounded; multiple stiff stems, upright to outright, arising from a dense base; flower heads freely branching; dense and full, resists developing an open center later in the season;

Growth rate: Moderately vigorous;

Plant size: About 27.0 cm tall and 42.0 cm wide in full flower;

Main stems: Glabrous; about 35 per plant; diameter at stem base about 6.5 mm, average about 5.0 mm; about 21.5 cm long from base to initial flower cymes; maintaining foliage to base of stem; internodes average about 7.0 mm;

Main stem color: Nearest RHS 146B; upper branched peduncle nearest RHS 148C maculate with between RHS 187B and RHS 187C;

Foliage: Opposite, simple; obovate to rhombic; smooth; glaucous and glabrous abaxial and adaxial; abaxial and adaxial surface matte; apex rounded and weakly serrate with five teeth; thick, fleshy and succulent; to about 62.0 mm long, about 28.0 mm across near apex, and about 2.5 mm thick, average about 56.0 mm long, about 18.0 mm wide, about 2.5 mm thick; decreasing in size distally;

Foliage color: Developing leaves—adaxial and abaxial surface between RHS N138B and RHS N138C; late season adaxial nearest RHS NN137A and abaxial nearest RHS NN137D;

Venation: Pinnate; color adaxial and adaxial midribs nearest RHS 146C, other veins same as surrounding leaf tissue on both surfaces;

Flower: Rotate; upright; perfect; actinomophic; in terminal compound cymes; freely flowering habit with up to 1000 per branched stem and 7,000 to 15,000 per plant, completely covering the entire foliage;

Flower size: About 12.0 mm across and 7.0 mm tall;

Flower facing: Mostly upwardly;

Flower fragrance: Not detected;

Flowering season: Beginning mid-August and continuing for about four weeks in Zeeland, Mich.;

Longevity: Individual flower remain effective for about four to six days on the plant; individual flowers persistent;

Flower buds about one day prior to opening: Conical; apex acute; base rounded; about 6.0 mm long and 4.0 mm across near middle;

Flower bud color: Exposed petals nearest RHS NN155C with heavy mottling of nearest RHS NN74B; calyx nearest RHS N138C with tinting of nearest RHS 187B toward apex;

Inflorescence: To about 8.0 cm tall from first branch and 12.0 cm across;

Petals: Typically five; lanceolate; narrowly acute apex, base truncate, margin entire, glabrous; typically about 7.0 mm long and about 2.5 mm across;

Petal color: Adaxial base lighter than RHS 75D, apical 0.5 mm nearest RHS NN74B with middle portion nearest blend between RHS NN74D and RHS 73D; abaxial lighter than RHS 75D lightly mottled with nearest RHS NN74B;

Calyx: Rotate; 4.0 mm across and 2.5 mm long;

Sepals: Typically five; lanceolate; entire; glabrous and glaucous abaxial and adaxial; narrowly acute apex, truncate fused base; about 2.7 mm long and about 0.7 mm wide at fused base;

Sepal color: Nearest RHS N138C both adaxial and abaxial surfaces;

Peduncles: Glabrous; cylindrical; strong and stiff, yet flexible; freely branching, compound branches to 8.0 cm long; angle erect in center to nearly 60 degrees from perpendicular for branched portions; flowering portion about 8.0 cm long and 12.0 cm across;

Peduncle color: Nearest RHS 146B; upper branched peduncle nearest RHS 148C maculate with between RHS 187B and RHS 187C;

Pedicels: Cylindrical; glabrous; glaucous to lustrous; strong and stiff, yet flexible; to about 7.0 mm long and 0.7 mm diameter; average about 5.0 mm long and RHS 0.7 mm diameter;

Pedicel color: Nearest blend of RHS N138D and RHS 191B;

Androecium: Stamens: typically five, rarely seven to ten;

*Filaments*.—Thin; terete; upright; fused to petal base; about 4.5 mm long and about 0.2 mm diameter; color nearest RHS 64C.

*Anthers*.—Ellipsoidal; basifixed; about 0.5 mm long and about 0.3 mm wide; color nearest RHS 61A.

*Pollen*.—Not observed; sterile.

Gynoecium: Typically five, rarely four; cylindrical, conic in distal one third; to 6.05 mm long;

*Style*.—About 1.0 mm long and 0.5 mm diameter near middle; glabrous; color nearest RHS 64A.

*Stigma*.—Minute about 0.2 mm across; color nearest 64A.

*Ovary*.—Nearly cylindrical, tapering at apex to style; about 4.5 mm long and 1.2 mm diameter at base; color nearest NN155B at base and distally nearest RHS 64A.

Seed and fruit: Sterile;

Disease and pest resistance: Plants of the new *Sedum* 'Pride and Joy' grow best with good drainage, full sun and moderate to low fertility. 'Pride and Joy' is cold hardy from USDA zones 3 to 9. 'Pride and Joy' tolerates heavy rains and wind and does not tend to develop an open center later in the season as many other stonecrop cultivars do. Other pest and disease resistance, tolerance and susceptibility outside that normal for Stonecrop is not known.

It is claimed:

1. A new and distinct perennial *Sedum* plant named 'Pride and Joy' as herein described and illustrated.

* * * * *